(12) United States Patent
Kitada et al.

(10) Patent No.: US 7,913,734 B2
(45) Date of Patent: Mar. 29, 2011

(54) METHOD AND SYSTEM FOR LAMINATING OPTICAL ELEMENTS

(75) Inventors: Kazuo Kitada, Osaka (JP); Yoshihiro Kameda, Osaka (JP); Kanji Nishida, Osaka (JP); Tomokazu Yura, Osaka (JP); Takaichi Amano, Osaka (JP); Hiromichi Ohashi, Osaka (JP); Atsushi Hino, Osaka (JP); Naoyuki Matsuo, Osaka (JP)

(73) Assignee: Nitto Denko Corporation, Osaka (JP)

( * ) Notice: Subject to any disclaimer, the term of this patent is extended or adjusted under 35 U.S.C. 154(b) by 0 days.

(21) Appl. No.: 12/843,430

(22) Filed: Jul. 26, 2010

(65) Prior Publication Data

US 2010/0288441 A1 Nov. 18, 2010

Related U.S. Application Data

(60) Division of application No. 12/422,907, filed on Apr. 13, 2009, and a continuation of application No. PCT/JP2007/069967, filed on Oct. 12, 2007.

(30) Foreign Application Priority Data

Oct. 17, 2006 (JP) ................................. 2006-282378
Aug. 13, 2007 (JP) ................................. 2007-211001
Oct. 12, 2007 (JP) ................................. 2007-266200

(51) Int. Cl.
*B32B 41/00* (2006.01)
(52) U.S. Cl. .......... 156/360; 156/361; 156/378; 156/379
(58) Field of Classification Search .................. 156/360, 156/361, 378, 379, 64, 252, 253
See application file for complete search history.

(56) References Cited

U.S. PATENT DOCUMENTS 6,592,693 B1* 7/2003 Nedblake ........................ 156/64
6,857,714 B2* 2/2005 Hohberger et al. ............... 347/2

FOREIGN PATENT DOCUMENTS

JP 55-120005 9/1980

(Continued)

OTHER PUBLICATIONS

English Translation of JP 2005-062165. Mar. 2005.*

(Continued)

*Primary Examiner* — George R Koch, III
(74) *Attorney, Agent, or Firm* — Lowe Hauptman Ham & Berner LLP

(57) ABSTRACT

A strip-shaped polarizing film has a protective film strip conformably adhered to one surface thereof and a releasable liner conformably adhered to the other surface thereof and delivered from a film delivering station 1. After an appearance inspection, a lamination of the protective film strip and the polarizing film strip F is half-cut using a laser unit 11 to form an array of laminations each consisting of a protective film and a polarizing film F, with the releasable liner being left intact. Then, the polarizing films F are fed to a peeling mechanism 4. The peeling mechanism 4 feeds a forwardmost one the polarizing films F to a laminating mechanism 5 while peeling off the releasable liner therefrom by a knife-edged member. The forwardmost polarizing film F is laminated to a liquid-crystal panel W conveyed to the laminating mechanism by a panel transport apparatus 18 in synchronization of the feeding of the forwardmost polarizing film F.

5 Claims, 11 Drawing Sheets

FOREIGN PATENT DOCUMENTS

| | | |
|---|---|---|
| JP | 57-052017 | 3/1982 |
| JP | 57-052018 | 3/1982 |
| JP | 57-052019 | 3/1982 |
| JP | 07-157186 | 6/1995 |
| JP | 2004-333647 | 11/2004 |
| JP | 2004-338408 | 12/2004 |
| JP | 2004-345354 | 12/2004 |
| JP | 2004-361741 | 12/2004 |
| JP | 2005-037416 | 2/2005 |
| JP | 2005-037417 | 2/2005 |
| JP | 2005-043384 | 2/2005 |
| JP | 2005062165 A * | 3/2005 |
| JP | 2005-114624 | 4/2005 |
| JP | 2005-305999 | 11/2005 |
| JP | 2005-306604 | 11/2005 |
| JP | 2005-309371 | 11/2005 |
| JP | 2005-347618 | 12/2005 |
| JP | 2007-140046 | 6/2007 |
| JP | 4361103 | 3/2009 |
| TW | 200514682 A | 5/2005 |

OTHER PUBLICATIONS

English Trnaslation of JP 2004-338408. Dec. 2004.*
International Search Report mailed Jan. 15, 2008 for PCT/JP2007/069967.
International Search Report mailed Nov. 6, 2007 for PCT/JP2007/069967.
Taiwanese office action for application No. 096138784, citing the attached reference(s).

* cited by examiner

METHOD AND SYSTEM FOR LAMINATING OPTICAL ELEMENTS

CROSS REFERENCE TO RELATED APPLICATION

RELATED APPLICATIONS

The present application is a continuation of International Application Number PCT/JP2007/069967 filed Oct. 12, 2007, and claims priority from Japanese Patent Application Number 2006-282378 filed on Oct. 17, 2006, Japanese Patent Application Number 2007-211001 filed on Aug. 13, 2007, and Japanese Patent Application Number 2007-266200 filed on Oct. 12, 2007, and is a divisional of U.S. Ser. No. 12/422,907, filed on Apr. 13, 2009, the disclosures of which are hereby incorporated by reference herein in their entirety.

TECHNICAL FIELD

The present invention relates to a method for laminating optical elements configured to automatically laminate optical elements, such as a polarizing film, a brightness enhancement film (reflecting polarizer film) or a phase difference film (retardation film), to a sheet-shaped body, such as a liquid-crystal panel, in a quick and accurate manner, and a system for carrying out the method.

BACKGROUND ART

A conventional system for laminating an optical element to a substrate in the form of a sheet-shaped body has been implemented as follows. A plurality of substrates are sequentially delivered at a given intervals on one hand, and on the other hand, a continuous-strip-shaped photosensitive laminate film comprising a photosensitive resin layer and a base film with a protective film laminated thereon is unwound from a stock roll while the protective film is removed from the photosensitive laminate film when the photosensitive laminate film is unwound, and thereafter the photosensitive laminate film is delivered together with the substrate into a nip between a pair of heat rollers where the photosensitive film and the substrate are bonded together under heat and pressure. Subsequently, the substrate having the photosensitive laminate film strip adhered thereto is cooled, and then only the photosensitive resin layer strip is cut (hereinafter referred as "half-cut") along leading and trailing edges of the substrate in a transfer direction of the substrate, the continuous strip of the base film being removed from the substrate and collected, and the substrate having the photosensitive resin layer laminated thereon is transferred to a subsequent processing station (refer to the following Patent Document 1).

[Patent Document 1] JP Hei 7-157186A

DISCLOSURE OF THE INVENTION

Problem to be Solved by the Invention

Further, in the conventional system, the substrate is conveyed to a subsequent station and handled under a condition that the photosensitive resin layer is exposed, which causes another problem of dust being adhered onto the exposed surface resulting in degradation in quality.

The present invention has been made in view of the above circumstances, and has a primary object of providing an optical element laminating method capable of automatically laminating an optical element to a sheet-shaped body in a quick and accurate manner, and a system for carrying out the method.

Means for Solving the Problem

In accordance with a first aspect of the present invention, there is provided a method of laminating an optical element to a sheet-shaped body, which comprises the steps of: providing an optical element strip which has a releasable liner conformably attached on a first one of opposite surfaces thereof; cutting the optical element strip at given intervals in a feed direction of the optical element strip with the releasable liner being intact; peeling off the releasable liner from a forwardmost one of the optical elements in a sequential manner; and laminating the forwardmost optical element to the sheet-shaped body through the exposed first surface thereof.

According to the above method of the present invention, the optical element strip is cut while leaving the releasable liner intact, so that the optical elements serially arrayed on the strip-shaped releasable liner and each formed in a desired sheet shape can be fed to a laminating position where the forwardmost one of the optical elements is laminated to the sheet-shaped body. In this way, the laminating process can be performed automatically and continuously, by peeling the releasable liner from a forwardmost one of optical elements in a sequential manner at the laminating station. Thus, there is no need to prepare an optical element punched out in a sheet shape conforming to that of a sheet-shaped body as a counterpart for forming an intended laminate structure, and thereby no need to transport an optical element to an independent laminating station. This makes it possible to drastically reduce a total time for a laminating process.

In accordance with a second aspect, in addition to the first aspect, the optical element strip further has a protective film strip conformably attached to the other, second surface thereof, wherein the step of cutting includes cutting a lamination of the protective film strip and the optical element strip at the given intervals in the feed direction with the releasable liner being left intact.

According to this feature, the lamination of the protective film strip and the optical element strip is cut while leaving the releasable liner intact, so that cut sheets of laminations are formed in the state that they are serially arrayed on the strip-shaped releasable liner whereby the cut sheets can be fed to the laminating station. In this way, the succeeding laminating process can be performed automatically and continuously, by peeling the releasable liner from a forwardmost one of the cut sheets of laminations in a sequential manner at the laminating position. Thus, there is no need to prepare an optical element punched out in a sheet shape conforming to that of a sheet-shaped body as a counterpart for forming an intended laminate structure, and thereby no need to transport an optical element to an independent laminating station. This makes it possible to drastically reduce a total time for a laminating process.

In addition, the protective film is kept attached on the optical element until the optical element is transported to a final station, to prevent dust from directly adhering to the surface of the optical element. This makes it possible to suppress occurrence of a defect due to dust being adhered the surface of the optical element and to maintain quality at a high level.

According to a further aspect of the present invention, in addition to the features described above, the cutting of the optical element strip or the lamination of the protective film strip and the optical element strip is performed by means of a laser beam.

According to this feature, the cutting process is free of which may otherwise be formed when cutting operation is carried out by using other type of cutting means, such as a cutting edge. In other words, it is possible to prevent any debris being adhered to the optical element strip. In addition, the optical element strip is not subjected to a pressing force which is generally applied thereto when the cutting operation is made using a cutter blade, so that it is possible to prevent any crack produced in the edge of the optical element cut by the cutting edge so as to eliminate a need for a post-process (finishing) for the cut edge.

In accordance with a further aspect of the present invention, the cutting of the optical element strip or the lamination of the protective film strip and the optical element strip by means of a laser beam is performed in such a manner that the optical axis of the laser beam is inclined with respect to a vertical direction from the forward side toward the backward side of a lateral scanning line of the laser beam as seen in the direction of movement of the strip.

When the laser beam is emitted for cutting operation to the optical element strip or the lamination of the protective film strip and the optical element strip, the optical element strip or the lamination is vaporized through thermal decomposition to cause a phenomenon similar to explosion. During this phenomenon, smoke is generated and spread out. For example, if a laser beam is emitted in a direction perpendicular to the surface of the optical element strip or the protective film strip, smoke is spread along the surface of the optical element strip or the protective film strip, to contaminate the surface.

Through extensive researches for suppressing the contamination of the optical element strip or the protective film strip due to the smoke, the inventors have carried out repeated experiments and arrived at the following findings.

If such operation of cutting the optical element strip is performed under a condition that an optical axis of a laser beam is set to be perpendicular to a cutting position of the optical element strip, or under a condition that an optical axis of a laser beam is inclined to extend from the backward side toward the forward side of the lateral scanning line of the laser beam, it is unable to suppress the contamination of the optical element strip, even under either of the above conditions. In contrast, when the cutting operation is performed with the optical axis of the laser beam inclined to extend from the forward side toward the backward side of the scanning line of the laser beam, as set forth above, the contamination of the optical element strip due to the smoke can be suppressed. Specifically, smoke generated during the cutting under the condition described above flows from the cutting position obliquely upwardly and backwardly without flowing along the surface of the optical element strip or the protective film strip while covering the surface.

More specifically, an angle between the optical axis of the laser beam and a reference axis perpendicular to the cutting position of the optical element strip should preferably be in the range of 10 to 45 degrees. The above described advantage of the method can be effectively obtained by setting the angle to fall within this range.

In accordance with a still further aspect of the present invention, the step of cutting includes, in the course of cutting the optical element strip or the lamination of the protective film strip and the optical element strip, a further step of blowing warm air toward a cutting position, simultaneously collecting and removing smoke generated during the cutting.

According to this feature, because of the warm air blown toward the cutting position, there will be an increase in temperature in the cutting position and its surrounding region. At the same time, gas or smoke generated during the cutting of the optical element strip or the lamination of the protective film strip and the optical element strip by means of the laser beam is carried with the stream of the warm air, and collected and removed. As a result, it becomes possible to prevent foreign debris from adhering to the cutting position and the surrounding region. This is based on the inventors' finding that foreign debris to be adhered to the cutting position and the surrounding region are formed in a course of cooling the gas (smoke) generated during the cutting, the finding having been obtained through various researches on factors causing contamination by foreign debris.

Specifically, the inventors have obtained knowledge that, while the optical element strip or the lamination of the protective film strip and the optical element strip is vaporized in the form of smoke by heat during irradiation of the laser beam, the smoke is cooled and liquidized under the influence of a surrounding member, for example, if a member for holding the sheet-shaped body during the cutting is made of a material, such as a metal, which is kept at a relatively low temperature even during the cutting at normal temperature, and the liquidized substances will be deposited again on the cutting position and the surrounding region to cause an adverse effect on quality.

According to still further aspect of the present invention, in addition to the features described above, the method further comprises, before the step of cutting, a step of inspecting the presence or absence of a defect in the optical element strip, wherein the releasable liner is detached from a portion of the optical element strip shortly before the inspection step is carried out, and the detached releasable liner or a new releasable liner is adhered to the portion of the optical element strip shortly after the portion of the optical element strip has subjected to the inspection step.

According to this feature, the defect in the optical element strip is detected in the inspecting step in advance of the cutting step. This makes it possible to adjustably prevent a defective portion of the optical element strip from being laminated to the sheet-shaped body. For example, in cases where an optical system is used in the inspecting step, the defect in the optical element strip is likely to be unable to be accurately detected, due to the influences of variation in orientation angle of the releasable liner, and reflected light from the releasable liner, in addition to the influence of variation in orientation angle of the optical element strip itself. For this reason, the releasable liner is detached shortly before the inspecting step. This makes it possible to eliminate an adverse effect of the releasable liner on the inspection so as to obtain a highly-accurate inspection result.

In accordance with still further aspect of the present invention, the step of cutting includes, when the defect in the optical element strip is detected through the step of inspecting, cutting a portion of the optical element strip including the defect, by a minimum distance, and the step of laminating includes peeling off the releasable liner from the defective optical element, and laminating the defective optical element to a strip-shaped collecting member, whereafter the collecting member is wound up to collect the defective optical element.

According to this feature, a region of the optical element strip including the defect can be cut by a minimum distance and collected. This makes it possible to effectively utilize the strip-shaped optical element.

The optical element in the present invention may be one selected from the group consisting of a film, a polarizing film for a liquid-crystal panel, and a reflecting polarizer film for a liquid-crystal panel. The sheet-shaped body in the present invention may be a liquid-crystal panel. Even if the optical element is a thin and flexible member, it can be laminated to the sheet-shaped body while preventing formation of crimp and trapping of air, because it is handled in a strip shape under a tension.

Still further, the present invention provides a system for laminating an optical element to a sheet-shaped body, which comprises: optical element feeding means operable to feed an optical element strip which has a releasable liner conformably adhered to a first one of opposite surfaces thereof; cutting means operable to cut the optical element strip at given intervals in a feed direction of the optical element strip with the releasable liner being left intact; peeling means operable to reverse the feed direction of the releasable liner along a knife-edged member to peel off the releasable liner from a forwardmost one of the optical elements in a sequential manner; transporting means operable to convey the sheet-shaped body to a position for laminating thereto the forwardmost one of the optical elements in a state after the releasable liner is peeled off therefrom; and laminating means operable to laminate the forwardmost optical element to the sheet-shaped body conveyed by the transporting means, through the exposed first surface thereof.

In the system of the present invention, the optical element strip fed by the optical element feeding means is cut into the array of optical elements with the releasable liner being left intact. This makes it possible to successively feed the optical elements each formed in a sheet shape conforming to that of the sheet-shaped body, to a laminating station through the medium of the strip-shaped releasable liner, and automatically laminate a forwardmost one of the optical elements to the sheet-shaped body in a sequential manner. Thus, this system can desirably implement the above method.

The optical element strip may further have a protective film strip conformably adhered to the other, second, surface thereof. In this case, the cutting means may be designed to cut a lamination of the protective film strip and the optical element strip at the given intervals in the feed direction to form an array of laminations each consisting of a protective film and the optical element, with the releasable liner being left intact.

Preferably, the cutting means is a laser unit. According to this feature, the cutting means based on the laser unit is free of risk of formation of debris which may otherwise be formed when the optical element strip is cut by means of other cutting means, such as a cutter blade or cutting edge. Thus, it is possible to prevent debris from being adhered to the optical element strip. In addition, the optical element strip becomes free from a pressing force which is otherwise applied thereto during an operation of cutting the optical element strip by pressing a cutter blade onto the strip. This makes it possible to prevent occurrence of crack in the edge of the optical element cut by the cutting means so as to eliminate a need for a post-process (finishing) for the cut edge.

Preferably, the laser unit is installed in an inclined posture to emit a laser beam in such a manner that an optical axis of the laser beam is inclined to extend from the forward side with respect to the scanning line of the laser beam toward the cutting position. More preferably, an angle between the optical axis of the laser beam and a reference axis perpendicular to the cutting position is in the range of 10 to 45 degrees. According to this feature, the previously described method can be desirably implemented.

According to a still further aspect, the system further includes air-blowing means operable, in the course of cutting the optical element strip or the lamination of the protective film strip and the optical element strip by the laser unit, to blow warm air toward the cutting position, and smoke-collecting/removing means operable to collect and remove smoke generated at the cutting position during the cutting.

According to this feature, warm air is blown from the air-blowing means toward the cutting position which is being cut by the laser unit, to prevent cooling of smoke generated from the cutting position. In addition, the generated gas or smoke is collected and removed by the smoke-collecting/removing means, to prevent liquidized substances from depositing on the surface of the optical element strip or the protective film. Thus, the previously described method can be desirably implemented.

According to a further aspect of the present invention, the system may further comprise: detaching means operable to detach the releasable liner from a portion of the optical element strip before the optical element strip is cut by the cutting means; inspection means operable to inspect the presence or absence of a defect in the portion of the optical element strip shortly after the releasable liner is detached from the portion of the optical element strip; and attaching means operable to attach the detached releasable liner or a new releasable liner onto the exposed first surface of the portion of the optical element strip shortly after the portion of the optical element strip has been inspected by the inspection means.

According to this feature, the releasable liner is detached from a portion of the optical element strip shortly before the portion of the optical element strip is inspected by the inspection means, so that the optical element strip can be inspected in a state wherein any adverse effect, such as variation in orientation angle and reflected light of the releasable liner, on the result of the inspection can be eliminated. In addition, the detached releasable liner or a new releasable liner is attached to the portion of the optical element strip shortly after the portion of the optical element strip has been inspected, so that the array of sheet-shaped optical elements cut by the cutting means can be successively fed to the laminating means through the medium of the strip-shaped releasable liner. Thus, the aforementioned method can be desirably implemented.

In accordance with a further aspect of the present invention, the laminating means may include: a laminating roller adapted to press a polarizing plate in the state after the releasable liner is peeled off therefrom; a first guide roller disposed in opposed relation to the laminating roller, and adapted to guide the sheet-shaped body conveyed by the transporting means and to be moved between a guide position for guiding the sheet-shaped body and a retracted position located below the guide position; and a second guide roller wound by a strip-shaped releasable member, and adapted to be moved to the guide position when the first guide roller is moved to the retracted position, wherein the system includes control means operable, when the defect in the portion of the optical element strip is detected by the inspection means, to control the cutting means to partially cut the optical element strip by a minimum distance including the defect, and, when the defective optical element is fed to the laminating means, to control the transporting means to stop transporting the sheet-shaped body, and control the laminating means to move the first guide roller to the retracted position and move the second guide roller to the guide position, so as to allow the defective optical element to be laminated to the releasable member on the second guide roller according to the laminating roller, and collected by rolling up the releasable member.

According to this feature, a region of the polarizing plate including the defect can be cut by a minimum distance and collected. This makes it possible to effectively utilize the strip-shaped polarizing plate.

Effect of the Invention

According to the optical element laminating method and the system for carrying out the method in accordance with the present invention, it is possible to perform the process including the step of cutting the optical element strip and laminating thus obtained optical element to the sheet-shaped body automatically in an efficient and accurate manner.

BEST MODE FOR CARRYING OUT THE INVENTION

The present invention will now be described with reference to an embodiment taking reference to the drawings. It should be noted that in the context of the present invention, the term "optical element" is not intended to be limited to a specific type, but it is intended to encompass any functional film of a flexible strip form, such as a polarizing film, a retardation film or a reflecting polarizer film, and an embodiment of the present invention will be described by way of example where a polarizing film is used as the optical element. In the present invention, the term "sheet-shaped body" is not intended to be limited to a specific type, but it is intended to encompass a liquid-crystal panel, a polarizing plate and any other sheet-shaped functional film, such as a polarizing film, a retardation film or a reflecting polarizer film. The following embodiment of the present invention will be described by taking as an example the case where a liquid-crystal panel is used as the sheet-shaped body.

In the context of the present invention, each of the terms "releasable liner" and "protective film" is intended to mean a material having a function of covering for protection an optical element to prevent damage of its surface. As used herein, the releasable liner is of such a type capable of being peeled and removed from an interface with an adhesive attached to an optical element, whereas the protective film is of such a type that is capable of being peeled and removed from an optical element strip together with an adhesive.

Figure 1:
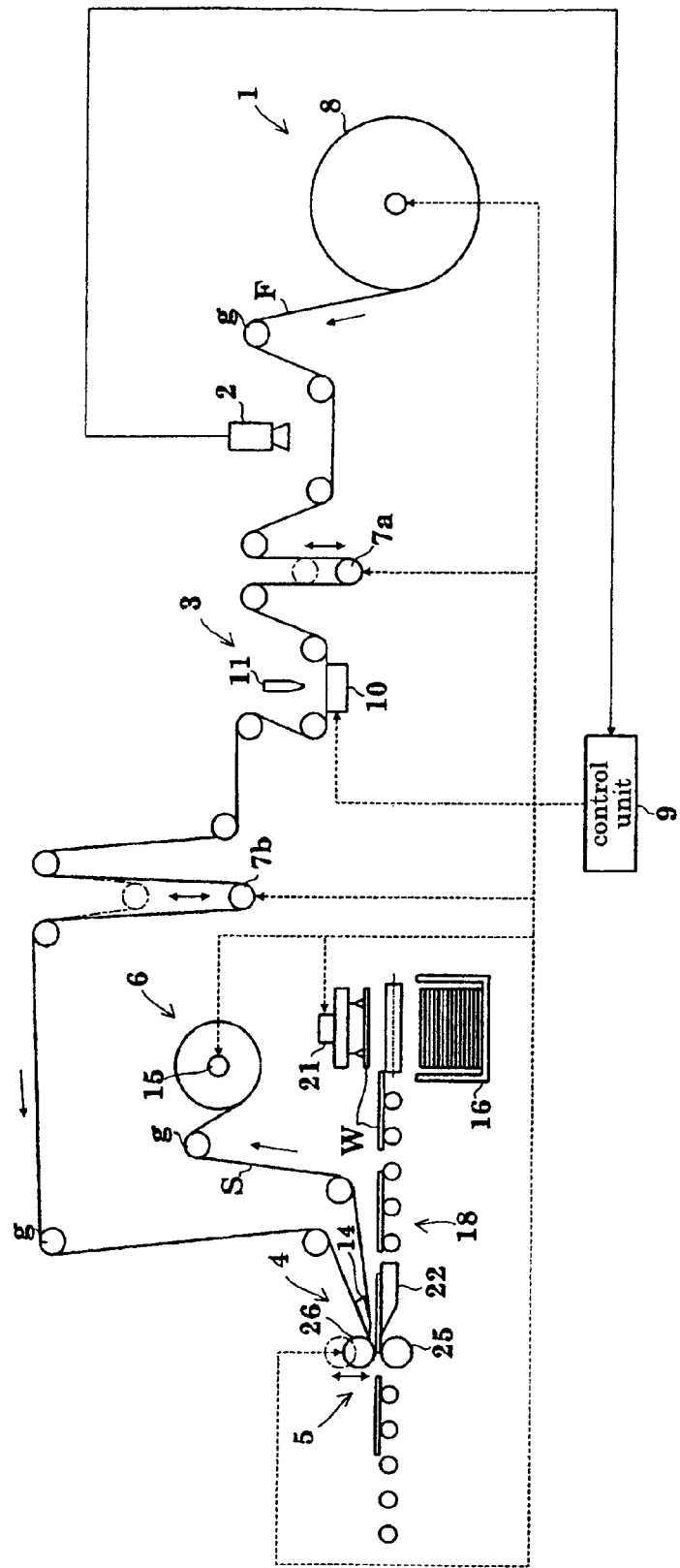
FIG. 1 is a schematic side view generally showing an optical element laminating system according to one embodiment of the present invention.

FIG. 1 schematically shows a configuration of an optical element laminating system implementing the optical element laminating method according to one embodiment of the present invention.

Figure 2:
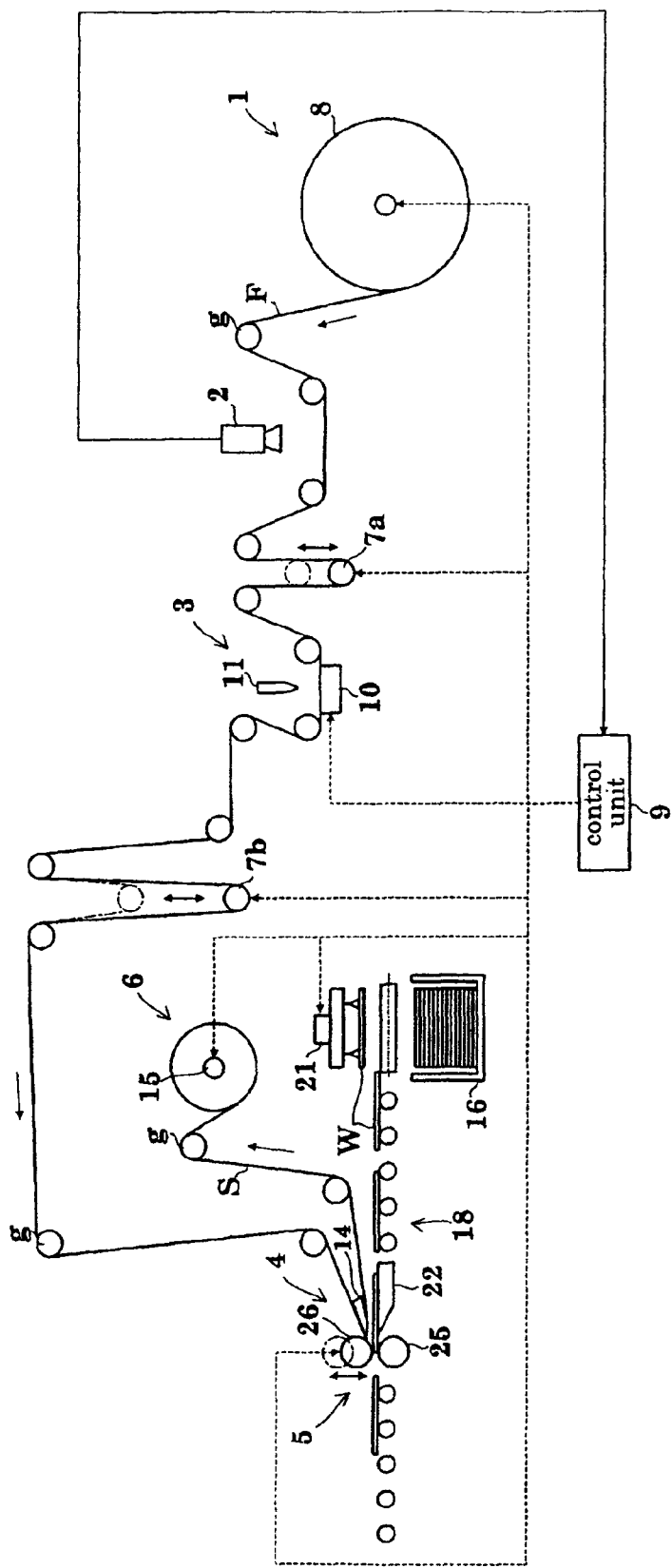
FIG. 2 is a top plan view generally showing a panel conveyance apparatus.

As shown in FIGS. 1 and 2, the system according to this embodiment is designed to feed a continuous strip of a polarizing film F to a laminating mechanism 5 for laminating a forwardmost one of the polarizing film sheets F to a liquid-crystal panel W in a sequential manner, and convey the liquid-crystal panel W to the laminating mechanism 5 via a first path which is provided separately from a second path through which the strip of the polarizing film F is passed.

As shown in FIG. 1, the feed path for the polarizing film F is provided with a film feeding section 1 from which the polarizing film F is unwound and delivered, the polarizing film strip F comprising a protective film P conformably adhered or attached to a first one of the opposite surfaces thereof and a releasable liner S conformably adhered or attached to the other, second surface thereof, an inspection unit 2 for carrying out an appearance inspection for the polarizing film F, a cutting mechanism 3 for cutting the polarizing film F to a given length in a feed direction to form an array of polarizing film sheets F, and a peeling mechanism 4 for peeling off the releasable liner S from a forwardmost one of the polarizing film sheets F while guiding a leading edge of the forwardmost polarizing film sheet F to the laminating mechanism 5, wherein the peeling mechanism 4 is located in a terminal end of the feed path for the polarizing film F. Further, a releasable-liner collecting section 6 is associated with the peeling mechanism 4 to wind up and collect the peeled releasable liner S. A plurality of guide rollers g and two dancer rollers 7a, 7b are appropriately interposed between respective ones of the above unit/sections/mechanisms. In regard to the correspondence relationship with elements of the appended claims, the film feeding section 1, the inspection unit 2, the cutting mechanism 3, the peeling mechanism 4, and the laminating mechanism 5, correspond to, but are not limited to, the optical element feeding means, the inspection means, the cutting means, the peeling means, and the laminating means, respectively.

The film feeding section 1 is loaded with a roll a continuous strip of a polarization film F prepared by longitudinally slitting a wider strip of polarization film F derived from a stock roll 8 into strips of a given width, the slit strip being wound into a roll.

The inspection unit 2 is designed to detect defects in the polarizing film F of the strip and foreign substances adhered to the surface of or existing in the polarizing film F, and in this embodiment, a CCD camera as an optical system is employed as the inspection unit 2. The CCD camera is disposed directly above the polarizing film strip F to image a portion of the polarizing film strip F passing therebeneath, continuously or intermittently. A result of the imaging is converted to a digital signal, and the digital signal is sent to a control unit 9 which will be described in detail later. Then, a processing section built in the control unit 9 is operable to perform a matching processing using a reference image acquired from a reference sample identical to an inspection target to detect crack/chip of the polarizing film strip F and attachment of foreign debris.

Figure 3:
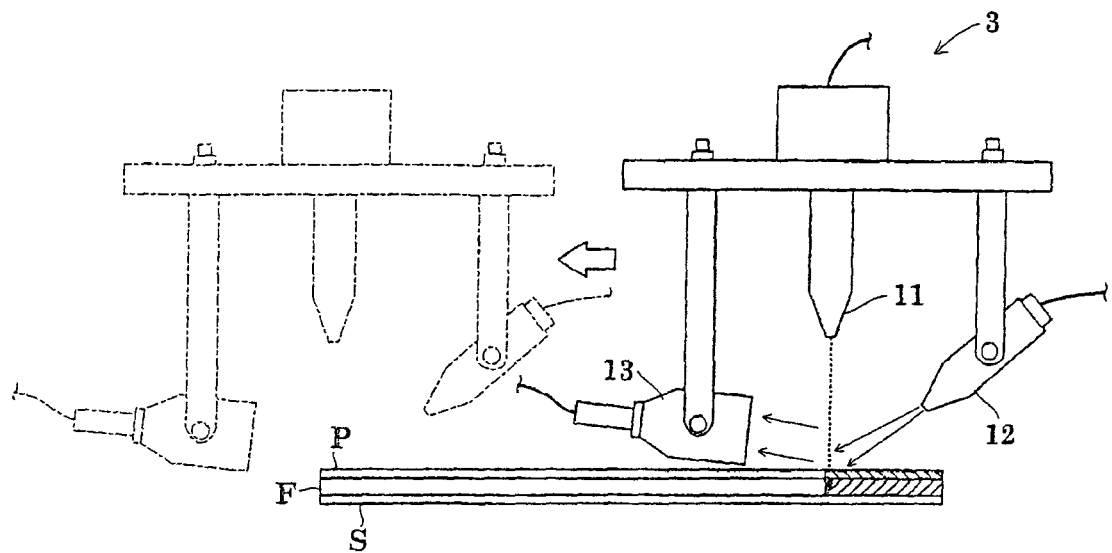
FIG. 3 is a schematic side view showing a cutting mechanism.

The cutting mechanism 3 comprises a holding table 10 for holding a portion of the polarizing film strip F under a suction pressure applied from a back surface thereof, and a laser unit 11 disposed directly above the portion of the polarizing film strip F. The laser unit 11 is adapted to be moved horizontally so as to scan a laser beam in a widthwise direction of the polarizing film strip F to cut the lamination of the polarizing film strip F and the protective film strip P at a given pitch in the feed direction, with the lowermost releasable liner being left intact (this cutting will hereinafter be referred as "half-cutting" when appropriate). As shown in FIG. 3, the laser unit 11 is integrally assembled with an air nozzle 12 for blowing warm air toward a cutting position of the polarizing film strip F, and a smoke collection duct 13 for collecting gas (smoke) generated from the cutting position and carried with a stream of the warm air, in such a manner that the air nozzle 12 and the smoke collection duct 13 are disposed on respective ones of opposite sides of the laser unit 11 in the widthwise direction of the polarizing film strip F and in opposed relation to each other. In regard to a correspondence relationship with elements of the appended claims, the air nozzle 12 and the smoke collection duct 13 correspond to, but are not limited to, the air-blowing means and the smoke-collecting/removing means, respectively.

The peeling mechanism 4 is provided at an end with a sharp-pointed knife-edged portion 14 which is adapted to provide a path of an acute angle for the releasable liner S by having the releasable liner S passed around the knife-edged portion 14, so as to peel the releasable liner S from the forwardmost one of the sheets of the polarizing film F while guiding the forwardmost polarizing film sheet F toward the laminating mechanism 5. Subsequently, the peeled apart releasable liner S is taken up by a collection bobbin 14 in the releasable-liner collecting section 6.

As shown in FIGS. 1 and 2, a plurality of liquid-crystal panels W to be conveyed via the second path are prepared by cutting a wide substrate into sheet-shaped pieces each having a given size, and loaded and stored as a stack in a liquid-crystal panel supply magazine 16 provided in a liquid-crystal panel supply section 17. Further, a dummy-substrate supply section 20 is provided in opposed relation to the liquid-crystal panel supply magazine 16 across a panel transport apparatus 18 for receiving and transporting the liquid-crystal panels W, wherein a plurality of dummy substrates DW are loaded and stored as a stack in a dummy-substrate supply magazine 19 provided in the dummy-substrate supply section 20.

Two vacuum suction-type pickup units 21 are disposed above the liquid-crystal panel supply section 17 and the dummy-substrate supply section 20, respectively, and each of the pickup units 21 is movable in a vertical direction and capable of reciprocating movement in a horizontal direction. Each of the pickup units 21 is adapted to hold under suction pressure the liquid-crystal panels W (dummy substrates DW) stored as a stack in the supply magazine 16 (19), one-by-one from the uppermost one.

The pickup unit 21 in the liquid-crystal panel supply section 17 is adapted to be moved upwardly and then forwardly while holding under suction pressure the liquid-crystal panel W, so as to transfer the liquid-crystal panel W to the panel transport apparatus 18 at a given position between the laminating mechanism 5 and the liquid-crystal panel supply section 17. The liquid-crystal panel supply magazine 16 is adapted to be controllably moved upwardly in conjunction with the unloading of the liquid-crystal panel W.

Similarly, the pickup unit 21 in the dummy-substrate supply section 20 is adapted to be moved upwardly and then forwardly while holding under suction pressure the dummy substrate DW, so as to transfer the dummy substrate DW to the panel transport apparatus 18 at a given position between the laminating mechanism 5 and the dummy-substrate supply section 20. The dummy-substrate supply magazine 20 is adapted to be controllably moved upwardly in conjunction with the unloading of the dummy substrate DW.

The panel transport apparatus 18 is designed to provide an upstream transport path for transporting the liquid-crystal panels W or the dummy substrates DW to the laminating mechanism 5, and a downstream transport path located downstream of the laminating mechanism 5 to convey the liquid-crystal panels W and the dummy substrate DW each subjected to a laminating operation. The upstream transport path is disposed beneath and in overlapped relation with a part of the feed path for feeding the polarizing films F half-cut by the cutting mechanism 3 to the laminating mechanism 5. The downstream transport path is divided into two sub-paths to separate the liquid-crystal panel W and the dummy substrate DW from each other. The panel transport apparatus 18 is formed as a roller conveyer in both the upstream and downstream transport paths.

Figure 4:
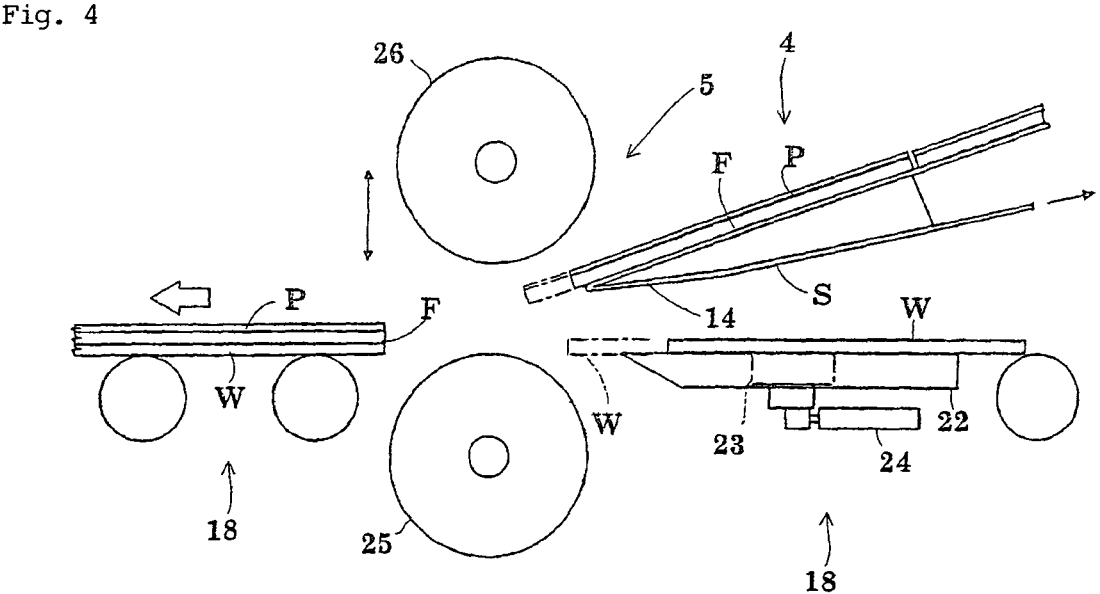
FIG. 4 is a schematic side view showing a peeling mechanism and a laminating mechanism.

As shown in FIGS. 2 and 4, there is provided a feed plate 22 just upstream side of the laminating mechanism 5. The feed device 22 is adapted to draw the liquid crystal panel W under a suction pressure and hold it with an appropriate suction force when a liquid crystal panel W is placed on its upper surface, by means of a sucking mechanism 23 through a rectangular opening formed in a central region of the feed plate 22, the sucking mechanism 23 being slidable forwardly and backwardly in a transport direction of the liquid-crystal panels W. Then, a cylinder 24 connected to a lower portion of the sucking mechanism 23 is activated to slidingly move the sucking mechanism 23 by a given stroke according to an extending or retracting movement thereof, so that the liquid-crystal panel W (dummy substrate DW) is fed forwardly along the upper surface of the support plate 22.

Based on the sliding forward movement of the sucking mechanism 23 by the given stroke, the liquid-crystal panel W can be moved forwardly beyond a forward edge of the knife-edged portion 14 and fed to a laminating position. The support plate 22 is fixedly installed such that its upper surface is located at a height position higher than an uppermost portion of an after-mentioned first guide roller 25 of the laminating mechanism 5 by an appropriate distance. The stroke of the cylinder 24 for slidingly moving the sucking mechanism 23 to feed the liquid-crystal panel W (dummy substrate DW) to the laminating position, and the height position of the upper surface of the feed plate 22, are appropriately determined depending on a size (including a thickness dimension), shape and material of the liquid-crystal panel W.

The laminating mechanism 5 comprises a guide roller 25 and a laminating roller 26. The guide roller 25 is comprised of a motor-driven rubber roller, and the laminating roller 26 comprised of a motor-driven metal roller is disposed immediately above the guide roller 25 for movement in the upward and downward directions, whereby, when the feed plate 22 is advanced to feed the liquid-crystal panel W to the laminating position, the laminating roller 26 is moved upwardly to a position higher than the upper surface of the feed plate 22 so as to provide an increased inter-roller gap. It should be understood that each of the guide roller 25 and the laminating roller 26 may be comprised of a rubber roller or may be comprised of a metal roller.

The control unit 9 is provided as a means to generally control a drive mechanism of the system according to this embodiment. Details of the control will be specifically described later in connection with a description about an operation of the system according to this embodiment. The structure and function of each of the major components of the optical element laminating system according to this embodiment are just like those described above. The following description will be made about a process of laminating each of the polarizing films F to a respective one of the liquid-crystal panels W, using the above system, with reference to FIGS. 1 to 7.

As shown in FIG. 1, the polarizing film F in the form of a continuous strip is fed out from the stock roll 8 loaded in the film feeding section 1, and fed to the inspection section 2 by being guided with a guide roll g. In the inspection section 2, an image of the polarizing film strip F is taken and digitized image data is sent to the control unit 9.

The control unit 9 functions to check the presence or absence of a defect or adhered foreign substance in the polarizing film strip F, based on a matching processing using the received image data and pre-acquired reference image data. After completion of the inspection, the polarizing film strip F is fed to the cutting mechanism 3 via the dancing roller 7a.

In the cutting mechanism 3, the delivered polarizing film F is held by the holding table 10 under a suction applied from a back surface of the table 10. During this operation, the control unit 9 controls the upstream dancer roller 7a to adequately maintain an operation of feeding the polarizing film strip F from the film feeding section 1. When the polarizing film strip F is thus held, the laser unit 11 is moved horizontally in a widthwise direction of the polarizing film strip F to cut the lamination of the polarizing film strip F and the protective film strip P, with the lowermost releasable liner being left intact. In conjunction with this half-cut operation, warm air is blown from the air nozzle 12 toward the cutting position of the lamination of the polarizing film strip F and the protective film strip P, and gas generated from the cutting position is collected and removed through the smoke collection duct 13.

After completion of the half-cut operation, the holding effort by the holding table 10 is temporarily released to allow the polarizing film strip F to be fed in the feed direction by a given distance, and then the polarizing film strip F is held again under a suction by the holding table 10. Then, the laser unit 11 performs a half-cutting operation for forming a trailing edge of the one polarizing film sheet F. At this instance, the polarizing film F is cut to a size equal to or less than that of the liquid-crystal panel W to which the polarizing film F is to be laminated, the cut sheet of the polarizing film being held adhered to the strip-shaped releasable liner S and feed to the peeling mechanism 4 by being guided by the guide rollers g and according to a movement of the dancer roller 7b.

Synchronized with the transportation of the polarizing film F to the laminating mechanism 5, the pickup unit 21 picks up an uppermost one of the liquid-crystal panels W from the liquid-crystal panel supply magazine 16 and transfers it to the panel transport apparatus 18. The liquid-crystal panel W is then conveyed by means of a conveyor to the laminating mechanism 5.

Figure 5:
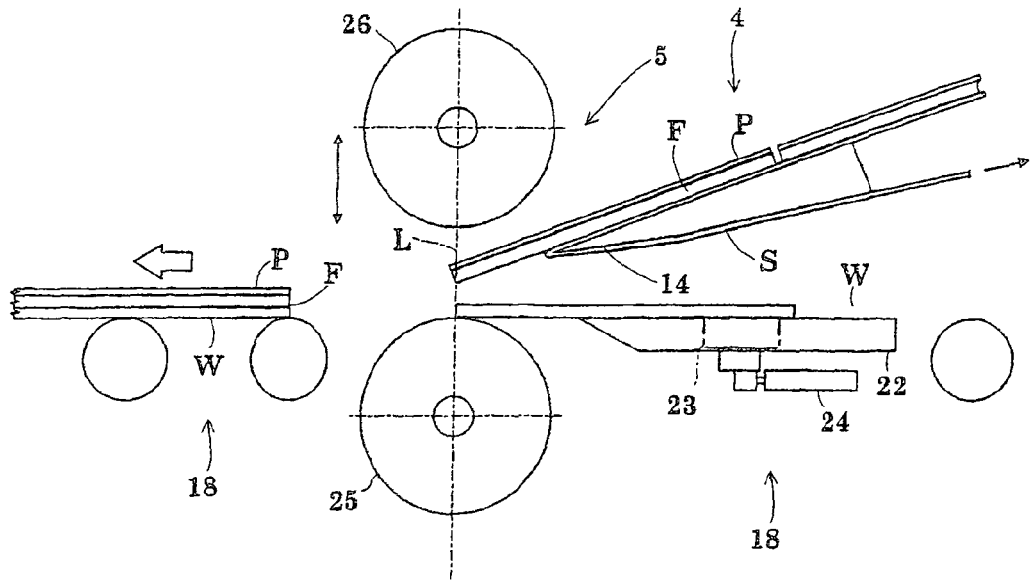
FIG. 5 is an explanatory diagram showing a polarizing film laminating operation.

As shown in FIG. 4, just before the laminating mechanism 5, the liquid-crystal panel W is transferred to the feed plate 22, and held under a suction pressure applied by the sucking mechanism 23 from the back surface thereof approximately at the same timing of the transfer operation. As shown in FIG. 5, the control unit 9 controls the operation of the cylinder 24 to feed the liquid-crystal panel W from the feed plate 22 to the guide roller 25, in a manner synchronized with the operation of feeding the leading edge of the forwardmost polarizing film F toward the gap between the laminating roller 26 in the retracted position and the first guide roller 25 in a fixed position, while reversing the feed direction of the releasable liner S along the knife-edged portion 14 of the peeling mechanism 4 to peel the releasable liner S off the forwardmost polarizing film sheet F. In this instance, the laminating roller 26 is moved upwardly to a position apart from the guide roller 25 by a given distance to increase the inter-roll gap, as mentioned above.

Figure 6:
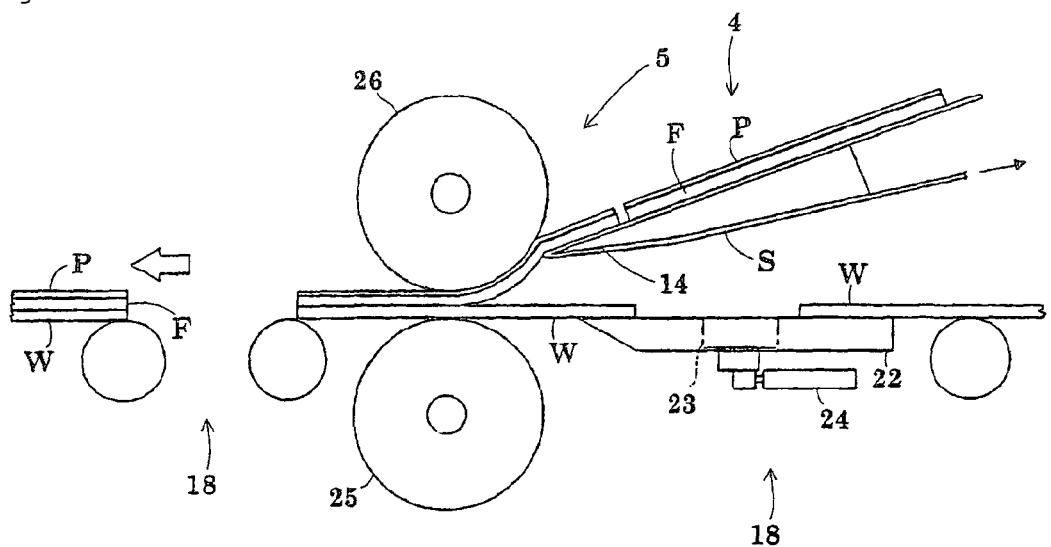
FIG. 6 is an explanatory diagram showing a polarizing film laminating operation.

When the leading edge of the forwardmost polarizing film F reaches approximately a line L passing through respective centers of the two rollers 25, 26 without contact with the guide roller 25, and when the leading edge of the liquid-crystal panel W reaches the line L, the control unit 9 controls the laminating mechanism 5 to move the laminating roller 26 toward the guide roller 25 by a given distance so as to press the forward portion of the forwardmost polarizing film F against the liquid-crystal panel W to allow the forwardmost polarizing film F to be laminated to the liquid-crystal panel W, as shown in FIG. 6. Generally, during this operation, the forwardmost polarizing film F is likely to be bendingly deformed in a chevron shape, due to a residual stress accumulated during the attachment of the releasable liner S and the protective film strip P and a peeling stress caused during the peeling of the releasable liner S. However, the forwardmost polarizing film F is correctively returned to its original flat shape while being pressed by the laminating roller 26, and pressed against and in parallel relation to an upper surface of the liquid-crystal panel W.

Then, along with the transport of the liquid-crystal panels W and the movement of the releasable liner S according to the wind-up operation, the polarizing film F detached from the strip-shaped releasable liner S will be continuously fed between the first guide roller 25 and the laminating roller 26 and laminated to the upper surface of the liquid-crystal panel W.

Then, when the trailing edge of the detached polarizing film F has passed through the nip of the two rollers and arrived at a predetermined position, the fact is detected, for example, by a rotary encoder or an optical sensor for detecting a predetermined rotational amount of the laminating roller 26 and/or the guide roller 25, the laminating roller 26 is moved away from the guide roller 25. The control unit 9 also controls the dancer roller 7b in synchronization with the laminating roller 26, the wind-up operation of the releasable-liner collecting section 6, and an activation and deactivation of the laminating mechanism 5, to allow the above series of operations to be adequately performed.

The liquid-crystal panel W with the polarizing film F laminated thereto is conveyed to a next station via the downstream transport path of the panel transport apparatus 18. In this manner, one cycle of laminating operation for the polarizing film F having no defect is completed.

Further, in cases where a defect in the polarizing film strip F and/or adhered foreign substance is detected by the inspection unit 2 during the above laminating operation, the following process will be performed.

When a defect, such as deficit portion is found in the polarizing film strip F by the inspection unit 2, a processing section built in the control unit 9 calculates a position coordinate of the defect based on image data acquired by the inspection unit 2, and controls to allow a defective polarizing film F including this defect to be laminated to the dummy substrate DW instead of being laminated to the liquid-crystal panel W, based on the calculated position coordinate. Specifically, a distance between a position of the polarizing film strip F at a timing of the detection of a defect, such as crack/chip, and the laminating mechanism 5, is known. Thus, the control unit 9 activates an encoder to count a rotational amount of a drive mechanism for feeding the polarizing film strip (polarizing films) F. Further, the control unit 9 calculates a timing when the defective polarizing film F reaches the laminating mechanism 5, and then operates to allow the dummy substrate DW to be transferred from the dummy-substrate supply section 20 to the panel transport apparatus 18, based on the calculation result. Then, when each of the defective polarizing film F and the dummy substrate DW reaches the laminating mechanism 5, a laminating operation is performed in the same manner as that for the non-defective polarizing film F, and the dummy substrate DW with the defective polarizing film F laminated thereto is conveyed via the downstream path in the panel transport apparatus 18. In this case, the dummy substrate DW with the defective polarizing film F laminated thereto is conveyed in a direction different from that for the non-defective polarizing film F at a branched position of the downstream path, and collected. In this manner, one cycle of a laminating operation using the dummy substrate DW is completed.

With a view to efficiently cutting and removing a portion of the polarizing film strip F having a defect, the following process may be performed. Given that the polarizing film sheet F to be laminated to the liquid-crystal panel W has a width Y of 476 mm and a length H of 836 mm, and if it is determined to be unable to half-cut the polarizing film strip F with this size, the position coordinate of the defect is calculated based on image data acquired by the inspection unit 2, and a trailing cut position is determined for defining a trailing edge of a defective polarizing film sheet to be formed at a position apart from the calculated position of the defect by a given length (in this example, 100 mm). Then, an inspection is conducted to determine if there is no defect within the distance (836 mm) from the trailing cut position for ensuring a non-defective sheet size of the polarizing film F.

Figure 7:
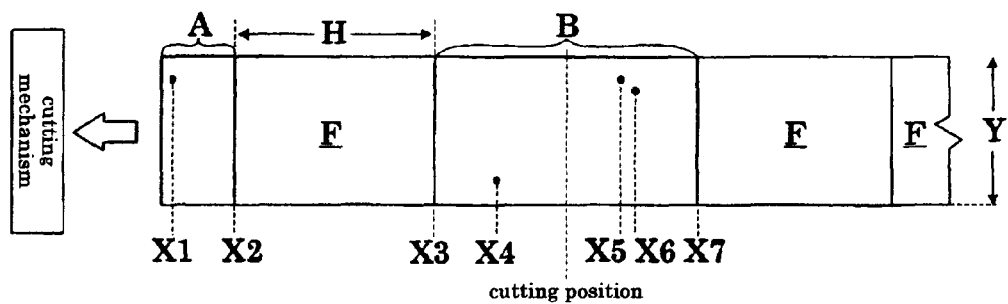
FIG. 7 is a diagram showing an operation of determining a cutting position of a polarizing film strip.

Specifically, after determining a margin from the position X1 of the defect to the cut position X2 as shown by A in FIG. 7, a further half-cut position X3 is determined if it is possible to ensure a length of a non-defective sheet of the polarizing film F.

In the case where, as shown in the area B in FIG. 7, a plurality of defects continuously exist at positions X4, X5, X6, and the length of the area covering these defects exceeds the length of the dummy substrate DW having the same size as the liquid crystal panel W, the area between the position X3 to the next cut position X7 is divided into a plurality of areas so that each divided area is within the size of the dummy substrate DW.

As mentioned above, in the course of feeding wherein the polarizing film strip F having the releasable liner S conformably adhered to the first surface thereof and the protective film strip P conformably adhered to the second surface thereof to the laminating mechanism 5, the lamination of the protective film strip P and the polarizing film strip F is half-cut by the laser unit 11 while leaving the releasable liner S intact, so that it is made possible to deliver sequentially arranged sheets of polarizing films F each having a size equal to or less than that of the liquid-crystal panel W, on the strip-shaped releasable liner S. Then, just before the laminating mechanism 5, the releasable liner S is peeled off from a forwardmost one of the polarizing film sheet F by reversing the feed direction of the releasable liner S along the knife-edged portion 14 of the peeling mechanism 4, while allowing the forwardmost polarizing film F to be fed to the laminating mechanism 5 and laminated to the liquid-crystal panel W.

Thus, the array of polarizing film sheets F each having approximately the same shape of that of the liquid-crystal panel can be fed substantially in the form of a strip and automatically laminated to respective ones of the liquid-crystal panels. Further, during this operation, the opposite surfaces of the polarizing film sheets F are covered respectively by the releasable liner S and the protective film strip, until the polarizing film sheet F is laminated to the corresponding liquid-crystal panel W, so that it is made possible to prevent contamination, such as dust, from attaching to the top and bottom surfaces of the polarizing film strip F. In addition, even after the laminating operation, the protective film P is still adhered to the surface of the polarizing film F to prevent dust from being adhered thereto.

It should further be noted that, during the operation of cutting the lamination of the polarizing film strip F and the protective film strip P by the laser unit 11, warm air is blown against a cutting position of the lamination, and gas generated during the cutting operation is collected and removed through the smoke collection duct 13, so that it is possible to prevent substances formed through cooling and liquidization of the gas from adhering to the cutting position and its surrounding region. Thus, it is possible to provide a liquid-crystal panel W with a non-defective polarizing film free of foreign substance.

The mechanism for blowing warm air against a cutting position during the half-cutting of the polarizing film strip F by the laser unit 11 and collecting/removing generated gas in the system according to the above embodiment will be more specifically described based on the following examples.

As shown in Table 1, in Example 1, warm air at 60° C. was blown from the air nozzle 12 against the cutting position of the polarizing film strip F while collecting and removing generated gas through the smoke collection dust 13.

In Example 2, the half-cutting operation based on the laser unit 11 was performed at an ambient air temperature without air-blowing and without collection/removal of generated gas. In Example 3, the half-cutting operation based on the laser unit 11 was performed at an ambient air temperature with only collecting and removing generated gas. In Example 4, under a condition that a room temperature is maintained at constant value of 25° C., warm air at the same temperature as the room temperature, i.e., 25° C., was blown against the cutting position while collecting and removing generated gas.

TABLE 1

| | Smoke collection | Air-blowing | Temperature | Width of attachment of foreign substance |
|---|---|---|---|---|
| EXAMPLE 1 | o*1 | o | 60° C. | Non |
| EXAMPLE 2 | x*2 | x | normal temperature | 9 mm |
| EXAMPLE 3 | o | x | normal temperature | 8 mm |
| EXAMPLE 4 | o | o | 25° C. | 2 mm |

*1 with the device
*2 without the device

As a result, as shown in Table 1, in Example 1, adherence of foreign substances was not observed in the cutting position and its surrounding region. In contrast, in Examples 2 to 4, adherence of foreign substances in a strip pattern with a certain width was observed around and on both sides of the cutting position. The widths of the adhered foreign substances in Example 2, Example 3 and Example 4 were 9 mm, 8 mm and 2 mm, respectively. That is, in either case devoid of blowing of warm air, adherence of foreign substances was observed on both sides of the cutting position.

From the above result, it was verified that the blowing of warm air toward the cutting position during the operation of cutting the polarizing film strip by the laser unit 11 can warm the cutting position and the surrounding region to prevent generated gas from being cooled and liquidized.

The above embodiment of the present invention may be modified as follows.

(1) The inspection unit 2 in the above embodiment may be designed such that a light source and a light-receiving element or a line sensor are disposed on respective ones of upper and lower sides of the polarizing film strip and in opposed relation to each other, to detect crack/chip of the polarizing film strip and attachment of foreign substance thereon, based on a change in intensity of light transmitted through the polarizing film strip being passing therebetween.

Figure 8:
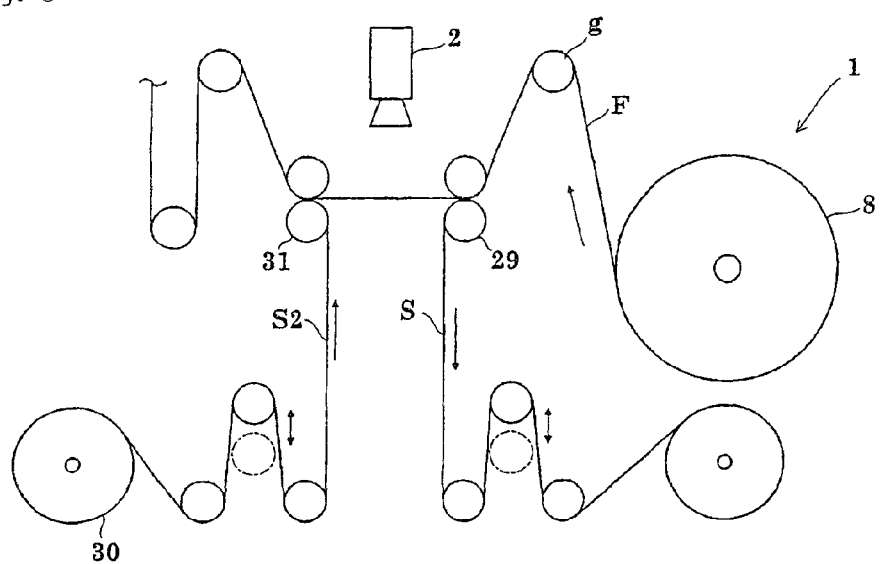
FIG. 8 is a schematic side view showing one example of a modified inspection section.

Further, as shown in FIG. 8, there may be provided a mechanism designed to detach the releasable liner S from a portion of the polarizing film strip by a detaching roller 29 just before the portion of the polarizing film strip is fed to the inspection section, and attach a new releasable liner S2 supplied from a roll 30 of the releasable liner S2, to the back side of the polarizing film strip F by means of an attaching roller 31.

According to the construction, it is possible in using the inspection unit 2 having an optical system described above to detect defects such as loss of specific optical feature with a high accuracy, by eliminating any adverse effect caused by for example variations in orientation of the releasable liner S and influence of reflected light. It should further be noted that the same releasable liner S detached from the polarizing film F may again be attached to the polarizing film F after the polarizing film strip F has been inspected.

Description will now be made with reference to the case where the inspection has been conducted after detaching the releasable liner S from the polarizing film F using the modified apparatus shown in FIG. 8 and the case where the inspection has been conducted with the releasable liner S attached to the polarizing film F, as specific examples.

In these examples, the inspection was performed under the following conditions. A laminate film has been prepared using films of T-VEGQ1724DU ARC15T-AC manufactured by Nitto Denko Corporation for the protective film strip P, the polarizing film strip F and the releasable liner S. This laminate film had a width of 1500 mm A line sensor camera having a resolution power of 30 µm, and a halogen lamp for illuminating a portion of the polarizing film strip F to be inspected, were used in the inspection unit 2. The feed speed of the polarizing film strip F was set at 50 m/min.

Based on the above inspection conditions, inspection has been conducted to detect respectively adherence of foreign substances on the surface of the polarizing film strip F or other film, and a knick which is a defect of a particular shape causing an optical distortion and having a dent-like configuration created by foreign debris being caught in or on the film during manufacturing process. For each of the polarizing film strip F from which the releasable liner strip S has been removed, and the polarizing film strip F with the releasable liner strip S attached thereto, the inspection has been conducted to detect a defect having a size of 100 µm or greater in a unit area of 560 mm×600 mm In the case of the polarizing film strip F from which the releasable liner strip S has been removed, 10000 locations in the unit area within the width of the laminate film strip has been inspected, and as a result, adherence of foreign substances could be detected at 560 locations.

In contrast, in the case of the polarizing film strip F with the releasable liner strip S attached thereto, adherence of foreign substances could be detected at 400 locations under the same condition.

Thus, given that an average number of detected locations in the case of the polarizing film strip F from which the releasable liner strip S has been removed is a detection rate of 100%, the detection rate in the case of the polarizing film strip F with the releasable liner strip S was (400/560)×100=71.4%.

In the same manner, as to the result of detection of knick, the defects were detected at 380 locations in the case of the polarizing film strip F having the releasable liner strip S removed, and detected at 354 locations in the case of the polarizing film strip F with the releasable liner strip S attached thereto. Thus, given that the detection result in the case of the polarizing film strip F having the releasable liner strip S removed is 100%, a knick detection rate in the case of the polarizing film strip F with the releasable liner strip S was 93.2%.

Figure 9:
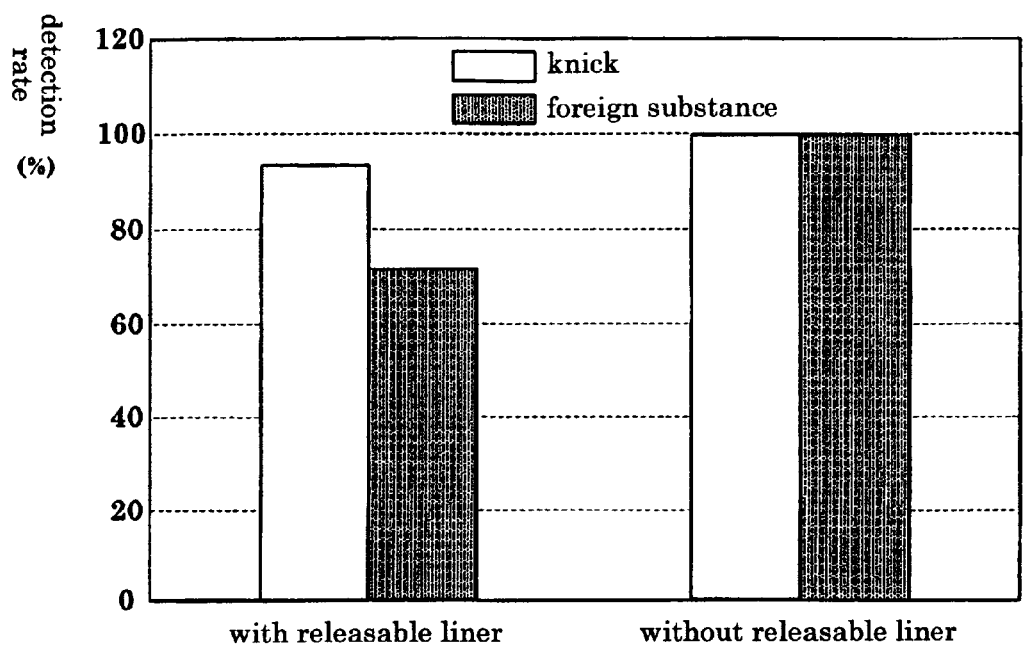
FIG. 9 is a graph showing an inspection result obtained by the modified inspection section.

FIG. 9 shows the above results. It should be noted that, a detection accuracy of foreign substances and the knick could be improved through the inspection of the polarizing film strip F after temporarily removing the releasable liner strip S therefrom. This makes it possible to laminate a high-quality polarizing film F to a liquid-crystal panel W.

(2) In the above embodiment, the defective polarizing film strip F is collected by being laminated on the dummy substrate DW, however, in an alternative way, the defective polarizing film may be collected by being laminated on a strip-shaped member.

Figure 10:
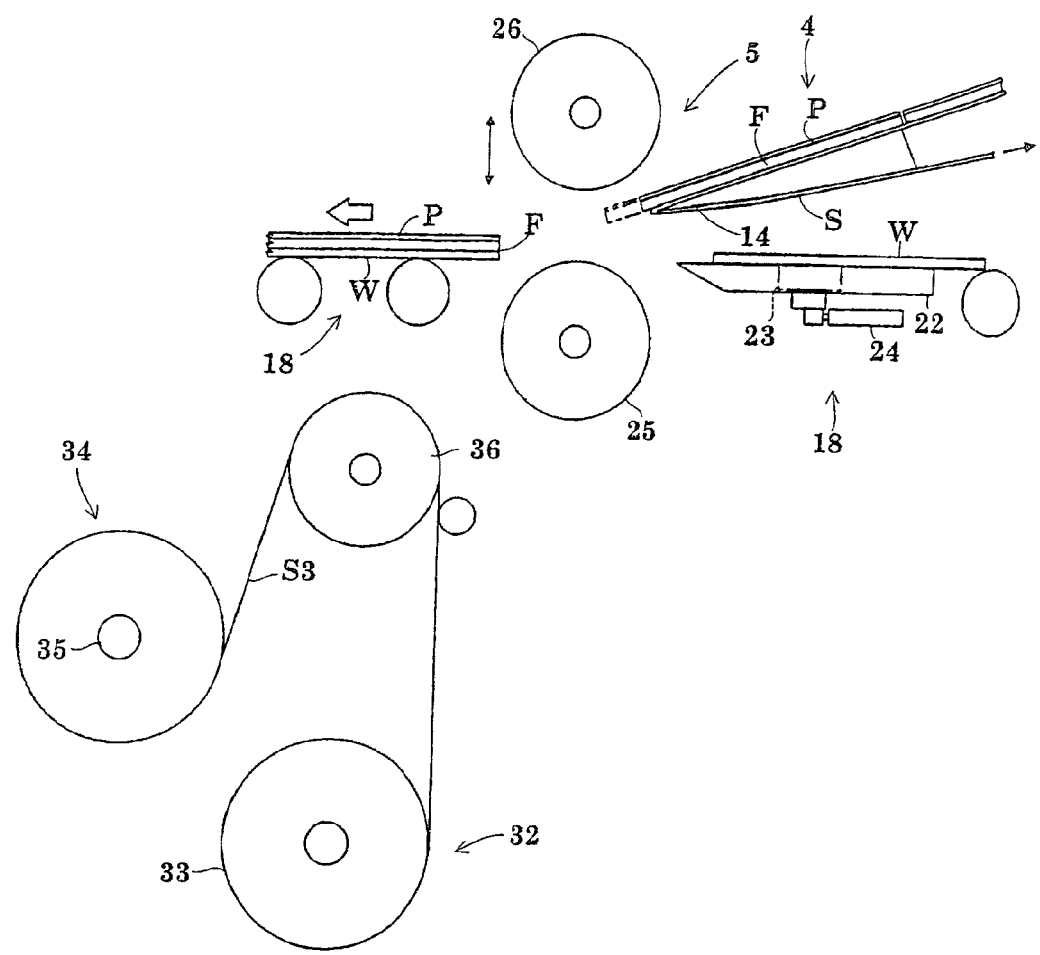
FIG. 10 is a schematic side view showing one example of a modified laminating mechanism.

For example, as shown in FIG. 10, the first guide roller 25 in the laminating mechanism 5 may be designed to be selectively moved in a vertical direction so as to increase a space for the laminating operation. Further, a second guide roller 36 may be disposed obliquely below the first guide roller 25 for bringing a strip-shaped member S3 unrolled from a stock roll 33 of the member S3 and passed around a collection bobbin 35 in a collecting section 34 to a position opposed to the laminating roller 26 for laminating the defective polarizing film F to the strip-shaped member S3.

Figure 11:
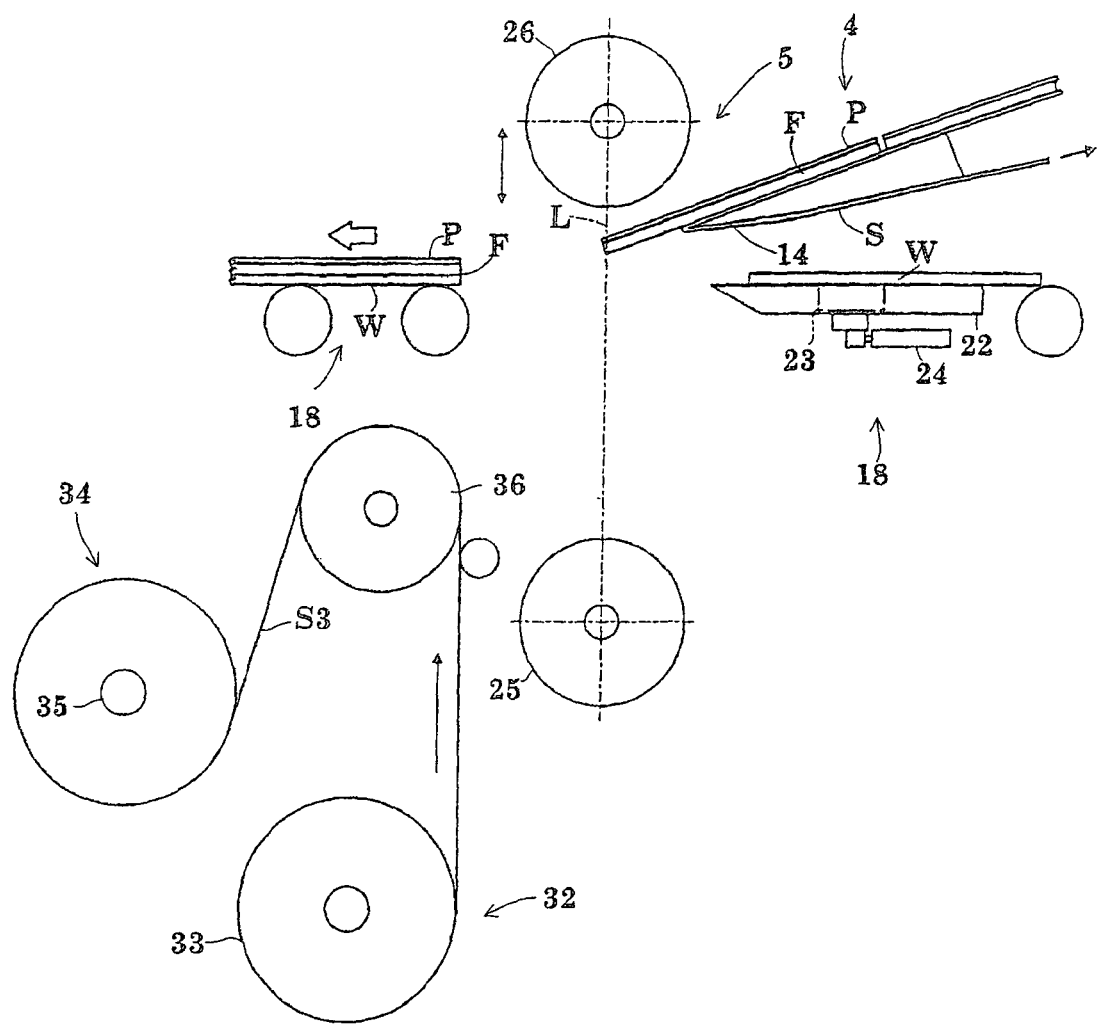
FIG. 11 is a schematic side view showing an operation of collecting a defective optical element in the modified laminating mechanism.
Figure 12:
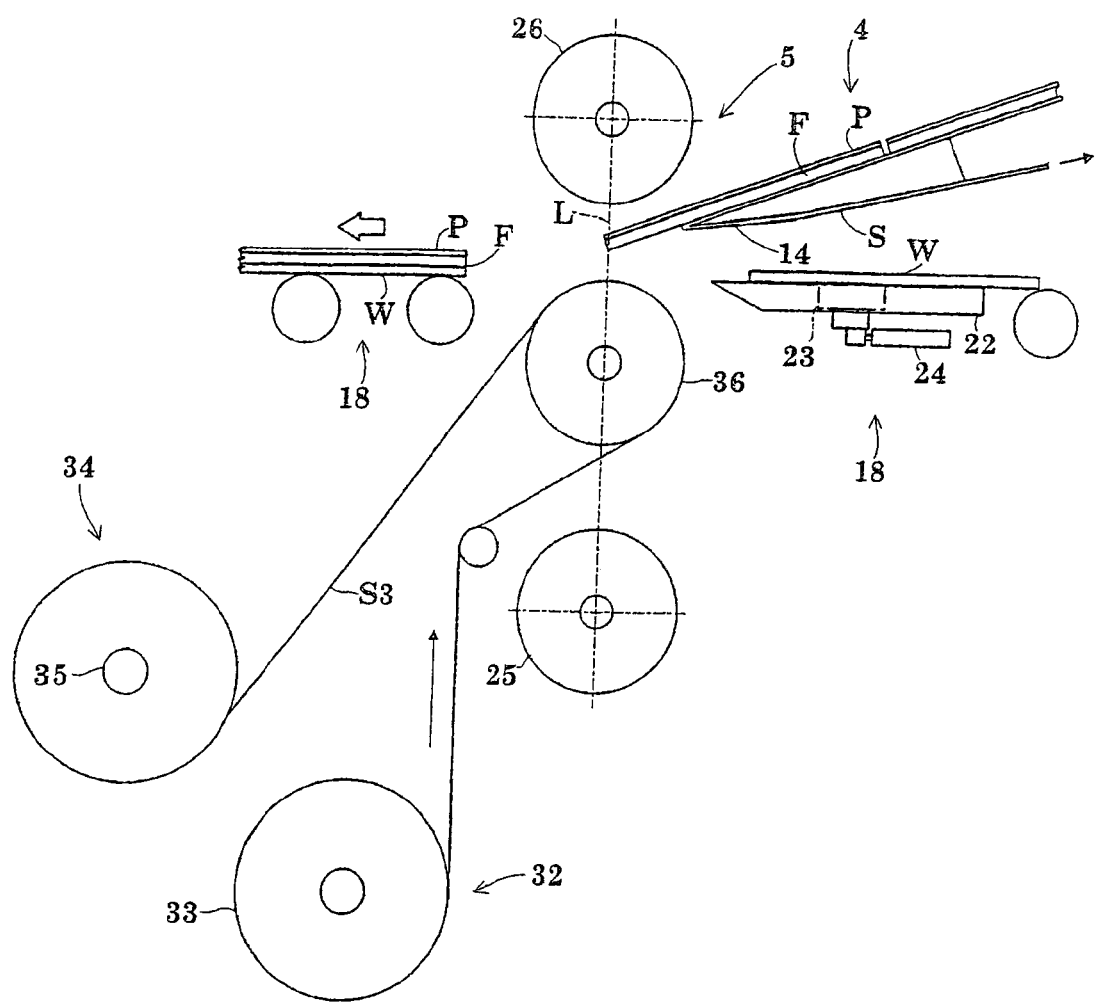
FIG. 12 is a schematic side view showing the operation of collecting a defective optical element in the modified laminating mechanism.
Figure 13:
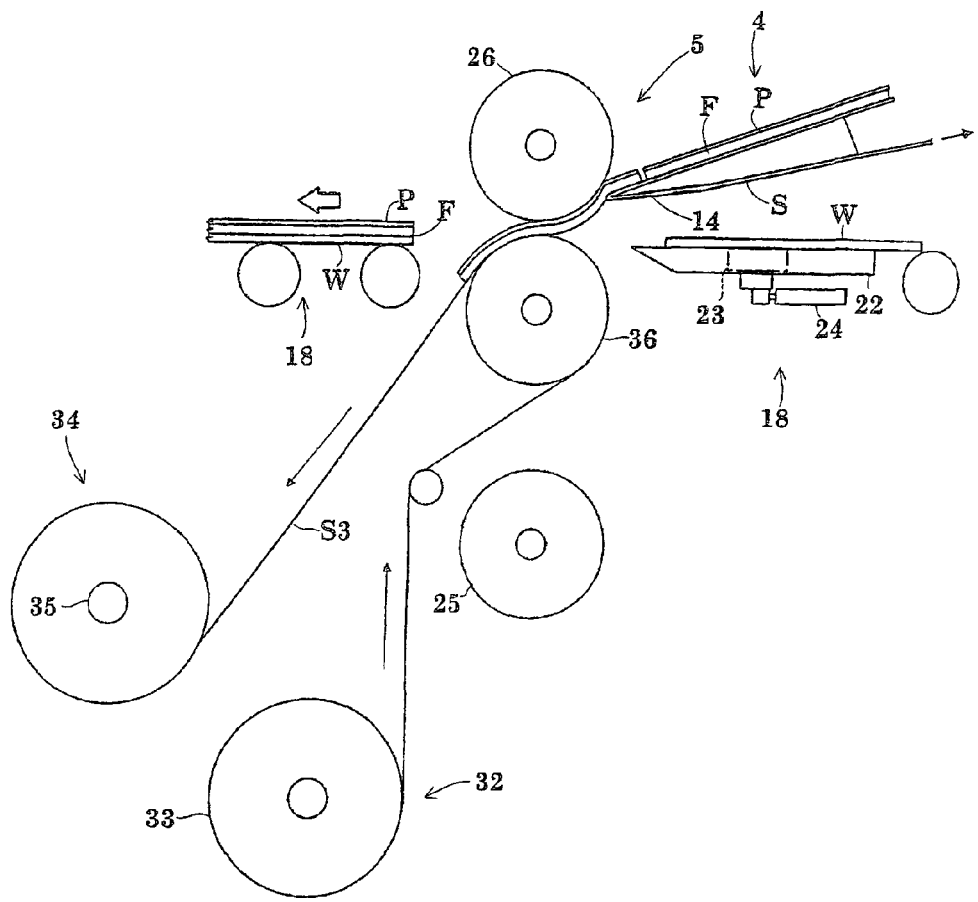
FIG. 13 is a schematic side view showing the operation of collecting a defective optical element in the modified laminating mechanism.

Specifically, when a defective polarizing film F is fed to the laminating mechanism 5, the first guide roller 25 is moved downwardly to increase the space below the laminating roller 26, as shown in FIG. 11, and then the second guide roller 36 is moved upwardly to the laminating position where the first guide roller 25 has been previously located, as shown in FIG. 12. Then, when the second guide roller 36 and the defective polarizing film F have reached the laminating position, the laminating roller 26 is moved downwardly to press and laminate the defective polarizing film F to the releasable member S3, as shown in FIG. 13. In synchronization with these movements, the releasable-liner collecting section 6 and the strip-shaped member collecting section 34 are operable to wind and collect the releasable liner S and the strip-shaped member S3, respectively.

Upon completion of the laminating operation for the defective polarizing film F, the second guide roller 36 is moved downwardly to return to a retracted position, and the first guide roller 25 is moved upwardly to return to the laminating position.

(3) Although the system according to the above embodiment employs the mechanism using the feed plate 22 to feed the leading edge of the liquid-crystal panel W, the present invention is not limited to such a mechanism, but any other suitable mechanism may be adopted as long as it is capable of accurately feeding the liquid-crystal panel W to the first guide roller 25. For example, the mechanism may be designed to convey the liquid-crystal panel W directly from the roller conveyer toward the first guide roller 25.

(4) In the above embodiment, when a laser beam is moved to scan in the widthwise direction of the polarizing film strip F, the optical axis of the laser beam is set to be perpendicular to the cutting position, however, in an alternative arrangement, the optical axis of the laser beam may be set as follows.

Figure 14:
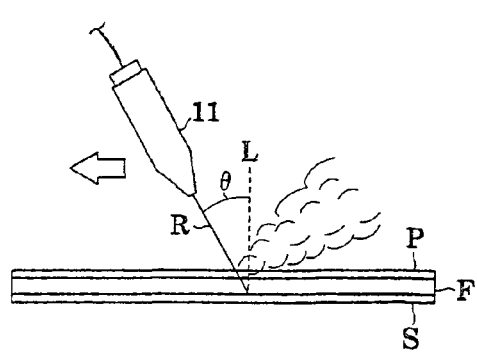
FIG. 14 is a fragmentary schematic side view showing one example of a modified cutting mechanism.

As shown in FIG. 14, the laser unit 11 may be installed in an inclined posture in such a manner that an optical axis R of the laser beam emitted from the unit is inclined to extend from the forward side of the transverse scanning line of the laser beam as seen in the longitudinal traveling direction of the polarizing film F toward the cutting position. In this case, an installation angle of the laser unit 11 is set such that an angle θ between the optical axis R of the laser beam and a reference axis perpendicular to the cutting position is in the range of 10 to 45 degrees. The installation angle θ is more preferably set in the range of 20 to 45 degrees, particularly preferably in the range of 30 to 45 degrees.

Figure 15:
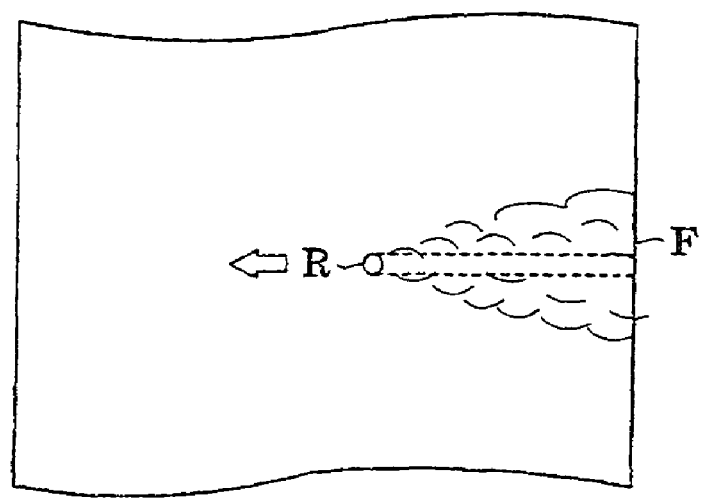
FIG. 15 is an explanatory top plan view showing a state of cutting using a laser beam in the modified cutting mechanism.

When the installation angle θ is set in the above range, smoke generated during cutting of the lamination of the polarizing film strip F and the protective film strip P flows from the cutting position obliquely upwardly and backwardly in the traveling direction, as shown in FIGS. 14 and 15. Thus, there is no risk of contamination in the cutting position and its surrounding region of a surface of the protective film strip P, which may otherwise be caused by adhesion of foreign debris arising from the smoke.

Figure 16:
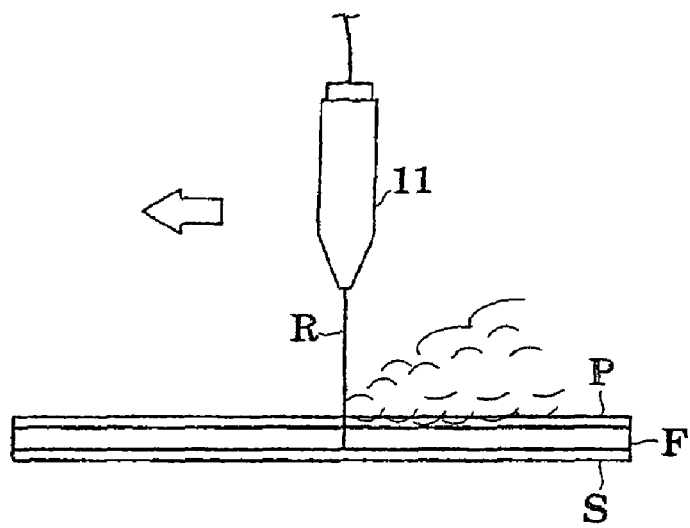
FIG. 16 is a side view showing a state of cutting using a laser beam in a cutting mechanism as a comparative example.

In contrast, if the installation angle θ is less than 10 degrees, for example zero degree as shown in FIG. 16, smoke generated during the cutting operation flows backwardly with respect to the scanning line of the laser beam in the traveling direction of the polarizing film F along the surface of the protective film strip P, so that the smoke is liable to cover the surface of the protective film strip P to cause adherence of foreign substances, resulting in a higher degree of contamination. When the laser unit 11 is installed in an inclined posture to emit the laser beam in such a manner that the optical axis R of the laser beam is inclined to extend from the rearward side of the laser scanning line as seen in the traveling direction toward the cutting position, smoke generated during the cutting operation flows along the surface of the protective film strip P, in the same manner as that in FIG. 16. This is also liable to result in a higher degree of contamination. If the installation angle θ is greater than 45 degree, an incident angle of the laser beam to the lamination of the polarizing film strip F and the protective film strip P becomes extremely small to cause deterioration in cutting accuracy.

Description will now be made with reference to specific examples where the laminations of the polarizing film strip F and the protective film strip P were half-cut under a condition that the installation angle θ of the laser unit 11 is changed among six different values. All the examples were performed under the same condition in cutting by the laser unit 11, wherein the laser unit 11 employed a carbon dioxide laser beam, and a laser wavelength, a spot size, a cutting rate and a laser power were set at 10.6 μm, 150 μm, 24 m/min and 32 W, respectively. The installations θ of the laser unit in Examples 5 to 11 were set at zero degree, 10 degrees, 15 degrees, 20 degrees, 30 degrees, 40 degrees and 45 degrees, respectively.

TABLE 2

|  | Angle (θ) | width of attachment (mm) |
| --- | --- | --- |
| Example 5 | 0 | 1.65 |
| Example 6 | 10 | 0.90 |
| Example 7 | 15 | 0.80 |
| Example 8 | 20 | 0.35 |
| Example 9 | 30 | 0.10 |
| Example 10 | 40 | Non |
| Example 11 | 45 | Non |

Observation has been made on the degree of contamination on the surface of the protective film P after cutting operation in each Example. As a result, the width (as measured in the traveling direction) of the area where foreign substances are adhered around the cutting position was 0.9 mm in the Example 6 and it has been observed that the width becomes smaller as the angle θ is increased in the order from the Example 7 to the Example 11. Particularly, in the Examples 10 and 11, no adherence of foreign substances was observed.

In contrast, as seen in Table 2, the width of the area having foreign substances adhered thereon in the Example 5 is 1.65 mm, and it has been recognized that the degree of contamination is almost two times greater than that in the other Examples 6 to 11.

As described above, the adherence of foreign substances at the cutting position and the surrounding region due to smoke generated during the cutting operation can be suppressed by installing the laser unit in an inclined posture in such a manner that the optical axis R of the laser beam is inclined to extend from a forward side in the traveling direction of the film relative to and toward the cutting position.

In place of a carbon dioxide laser beam, any other suitable laser beam may be appropriately adopted depending on an intended purpose. For example, a YAG laser beam or a UV laser beam may be used.

(5) In each of the above embodiments, use has been made of a polarizing film strip having a releasable liner S conformably adhered to a first surface thereof and a protective film strip P conformably adhered to the other, second surface thereof, however, it is possible to use a polarizing film strip having only such releasable liner S on one face but having no protective film strip P on the other face. In using such polarizing film strip, the apparatus shown in FIGS. 3 to 6 and FIGS. 10 to 16 may be used to laminate a polarizing film F on a liquid crystal panel W simply by eliminating the protective film P from the embodiments in these drawings.

INDUSTRIAL APPLICABILITY

As above, the present invention is suitable for use in automatically laminating an optical element cut to a given length, to a sheet-shaped body.

What is claimed is:

1. An apparatus for inspecting continuous film laminate including an optically functional continuous film having a releasable film adhered to one of the opposite sides thereof, or including an optically functional continuous film having a releasable film adhered to one of the opposite sides thereof and a protective film adhered to the other side thereof, for a presence of any defect in said optically functional continuous film, and making the film laminate usable in a laminating apparatus for laminating the optically functional continuous film to a product panel, the apparatus comprising:
   a delivering device for unwinding the continuous film laminate from a roll and delivering the laminate toward an inspection station;

a releasing device for releasing the releasable film from the film laminate before the film laminate reaches the inspection station;

an inspection device in the inspection station for inspecting the optically functional continuous film from which the releasable film is released for the presence of any defect;

a control device for calculating a coordinate position of a defect if such defect has been detected; and a releasable film laminating device for unwinding a releasable film from a roll and laminating the unwound releasable film to said one side of the optically functional continuous film after the inspection has been completed.

2. An apparatus in accordance with claim 1 further including an optical film laminating device located downstream side of the releasable film laminating device for laminating an optically functional film to a product panel member.

3. An apparatus adapted to use a continuous film laminate including an optically functional continuous film at least having a releasable film releasably adhered to one of the opposite sides thereof, and for providing sheets of optically functional film each having a predetermined length by at least partially cutting said optically functional continuous film, and laminating said sheets of optically functional film to corresponding ones of product panels; the apparatus comprising:

a cutting device for cutting said continuous film laminate along cutting lines extending transversely across said continuous film laminate, said cutting device adapted to cut said continuous film laminate at cutting lines spaced apart each other in a longitudinal direction by a distance corresponding to one of dimensions of said product panel, said cutting device positioned to cut said continuous film laminate from a side opposite to the side where said releasable film is adhered, said cutting device adapted to cut said continuous film laminate to a depth reaching an interface between said optically functional continuous film and said releasable film so as to define a sheet of optically functional film between each two longitudinally adjacent cutting lines between which no defect is detected by optical inspection, and to define a sheet of optically functional film with defect between each two longitudinally adjacent cutting lines between which at least one defect is detected by optical inspection;

a releasing device positioned to release said sheet of optically functional film from said releasable film after said continuous film laminate is cut by the cutting device by advancing said releasable film along an acute angle path where said releasable film is reversed in its direction of movement;

a panel delivering device for delivering a product panel to said laminating station so that the product panel is registered with the sheet of optically functional film released from said releasable film;

a laminating device for laminating said sheet of optically functional film to said product panel by pressing said sheet of optically functional film to said product panel; and a control system that calculates a time difference between a time of detecting the sheet of optically functional film with defect and a time of discarding the sheet of optically functional film with defect.

4. An apparatus adapted to use a continuous film laminate including an optically functional continuous film at least having a releasable film releasably adhered to one of the opposite sides thereof, and for providing sheets of optically functional film each having a predetermined length by at least partially cutting said optically functional continuous film, and laminating said sheets of optically functional film to corresponding ones of product panels; said apparatus comprising:

an inspection device for inspecting said continuous film laminate for a presence of any defect in said optically functional film while it is moved through the inspection device;

a control device for calculating a coordinate position of a defect when such defect is detected, said control device being operable to determine cutting lines extending transversely across said continuous film laminate, said cutting lines being spaced apart each other in a longitudinal direction of said continuous film laminate by a distance corresponding to one of dimensions of said product panel;

a cutting device for cutting sequentially said continuous film laminate along said cutting lines, said continuous film laminate being cut from a side opposite to the side where said releasable film is adhered, to a depth reaching an interface between said optically functional film and said releasable film so as to define a sheet of optically functional film between two longitudinally adjacent cutting lines, said control device being operable to classify the sheet of optically functional film containing the defect as a defective sheet, the remaining sheets as non-defective sheets, said control device being further operable to determine if the coordinate position of the defect is located between two longitudinally adjacent cutting lines, and if the coordinate position of the defect is located between said longitudinally adjacent cutting lines, to determine another cutting line at a position a predetermined distance apart toward upstream side from said coordinate position of the defect, for substitution for the upstream side one of said two longitudinally adjacent cutting lines;

a transporting device for transporting the continuous film laminate from the cutting device to a laminating station;

a releasing device for releasing said sheet of optically functional film from said releasable film at said laminating station by advancing said releasable film along an acute angle path where said releasable film is reversed in its direction of movement;

a product panel delivering device for delivering a product panel to said laminating station when a non-defective sheet of optically functional film is transported to the laminating station so that the product panel is registered with the non-defective sheet of optically functional film released from said releasable film; and a laminating device for laminating said non-defective sheet of optically functional film to said product panel by pressing said sheet of optically functional film to said product panel.

5. An apparatus in accordance with claim 4 further including a releasable film releasing device provided upstream of said inspection device for releasing said releasable film from said optically functional film prior to inspection, and a releasable film laminating device provided downstream of said inspection device for laminating a releasable film to said optically functional film after inspection.

* * * * *